(12) United States Patent
Tang et al.

(10) Patent No.: US 11,227,399 B2
(45) Date of Patent: Jan. 18, 2022

(54) ANALYSIS APPARATUS, ULTRASOUND DIAGNOSTIC APPARATUS, AND ANALYSIS METHOD

(71) Applicant: Canon Medical Systems Corporation, Otawara (JP)

(72) Inventors: Zhe Tang, Chaoyang (CN); Qi Chen, Chaoyang (CN); Weijian Jian, Chaoyang (CN); Yu Chen, Chaoyang (CN)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 114 days.

(21) Appl. No.: 16/577,034

(22) Filed: Sep. 20, 2019

(65) Prior Publication Data

US 2020/0098120 A1 Mar. 26, 2020

(30) Foreign Application Priority Data

Sep. 21, 2018 (CN) .......................... 201811107299.5
Sep. 20, 2019 (JP) ............................. JP2019-171125

(51) Int. Cl.
    *G06T 7/33* (2017.01)
    *G06T 7/00* (2017.01)
    *A61B 8/08* (2006.01)

(52) U.S. Cl.
    CPC ............ *G06T 7/337* (2017.01); *A61B 8/5207* (2013.01); *A61B 8/5261* (2013.01);
(Continued)

(58) Field of Classification Search
    CPC ..... A61B 8/483; A61B 8/5207; A61B 8/5261; G06T 7/0016; G06T 7/33; G06T 7/0014;
(Continued)

(56) References Cited

U.S. PATENT DOCUMENTS

| 8,111,892 | B2 | 2/2012 | Hyun et al. |
| 2004/0006273 | A1* | 1/2004 | Kim .................... G01S 15/8977 600/443 |

(Continued)

FOREIGN PATENT DOCUMENTS

JP    2006-217939 A    8/2006

*Primary Examiner* — Brenda C Bernardi
(74) *Attorney, Agent, or Firm* — Oblon, McClelland, Maier & Neustadt, L.L.P.

(57) ABSTRACT

An analysis apparatus according to an embodiment includes processing circuitry. The processing circuitry performs registration between first ultrasound image data obtained at a first phase by an ultrasound diagnostic apparatus and first medical image data obtained by a medical image diagnostic apparatus other than the ultrasound diagnostic apparatus and performs registration between the first ultrasound image data and second ultrasound image data obtained at a second phase different from the first phase by the ultrasound diagnostic apparatus, to generate second medical image data registered with the second ultrasound image data; and combines the second ultrasound image data and the second medical image data to generate a single image, thereby performing registration between ultrasound image data by the ultrasound diagnostic apparatus and medical image data by the medical image diagnostic apparatus.

8 Claims, 5 Drawing Sheets

(52) U.S. Cl.
CPC .. *G06T 7/0014* (2013.01); *G06T 2207/10132* (2013.01); *G06T 2207/20221* (2013.01)

(58) Field of Classification Search
CPC ........... G06T 7/337; G06T 2207/10081; G06T 2207/20221; G06T 2207/10088; G06T 2207/10132
See application file for complete search history.

(56) References Cited

U.S. PATENT DOCUMENTS

| | | | |
|---|---|---|---|
| 2009/0041323 A1* | 2/2009 | Lachaine | G06T 3/4007 382/131 |
| 2009/0275831 A1* | 11/2009 | Hall | G06T 7/38 600/437 |
| 2009/0303252 A1* | 12/2009 | Hyun | G06T 7/33 345/643 |
| 2016/0125605 A1* | 5/2016 | Lee | A61B 8/085 382/131 |
| 2017/0103540 A1* | 4/2017 | Brokman | A61B 5/055 |
| 2019/0343489 A1* | 11/2019 | Matsunaga | A61B 8/5261 |
| 2021/0068790 A1* | 3/2021 | Dufour | A61B 8/5276 |

* cited by examiner

ANALYSIS APPARATUS, ULTRASOUND DIAGNOSTIC APPARATUS, AND ANALYSIS METHOD

CROSS-REFERENCE TO RELATED APPLICATIONS

This application is based upon and claims the benefit of priority from Chinese Patent Application No. 201811107299.5, filed on Sep. 21, 2018 and Japanese Patent Application No. 2019-171125, filed on Sep. 20, 2019; the entire contents of which are incorporated herein by reference.

FIELD

Embodiments described herein relate generally to an analysis apparatus, an ultrasound diagnosis apparatus, and an analysis method.

BACKGROUND

An ultrasound diagnostic apparatus scan can observe the motion and function of tissues in real time and dynamically and can track lesions and display stereoscopic changes without being limited by their imaging stratification. Moreover, ultrasound devices have the advantages that they are easy to move, cause less damage to patients, and are low cost. However, an ultrasound diagnostic apparatus is sometimes less advantageous to other medical image diagnostic apparatuses in terms of resolution and sharpness and the like.

On the other hand, an example of a medical image diagnostic apparatus other than the ultrasound diagnostic apparatus includes an MRI (Magnetic resonance imaging apparatus). Using an MRI, it is possible to realistically display the anatomical structures and clearly display both diseased tissues and normal tissues and to obtain high contrast resolution of soft tissues. However, medical image diagnostic apparatus such as a CT (Computed Tomography) apparatus and an MRI apparatus is expensive, complicated in imaging, and have a long scan period, making it difficult for physicians to observe organs or biological tissues of the examined subject in real time.

In this regard, by registering an ultrasound image and an image obtained from other medical image diagnostic apparatus, such as a CT apparatus and an MRI apparatus and the like, it becomes possible to generate a combined image making full use of each of the images.

DETAILED DESCRIPTION

An analysis apparatus according to an embodiment includes processing circuitry. The processing circuitry performs registration between first ultrasound image data obtained at a first phase by an ultrasound diagnostic apparatus and first medical image data obtained by a medical image diagnostic apparatus other than the ultrasound diagnostic apparatus and performs registration between the first ultrasound image data and second ultrasound image data obtained at a second phase different from the first phase by the ultrasound diagnostic apparatus, to generate second medical image data registered with the second ultrasound image data; and combines the second ultrasound image data and the second medical image data to generate a single image, thereby performing registration between ultrasound image data by the ultrasound diagnostic apparatus and medical image data by the medical image diagnostic apparatus.

With reference to drawings, an analysis apparatus, an ultrasound diagnostic apparatus and a analysis method according to an embodiment will be explained below. Here, the same numerals are assigned for the same components and duplicate explanations will be omitted.

First Embodiment

Figure 1:
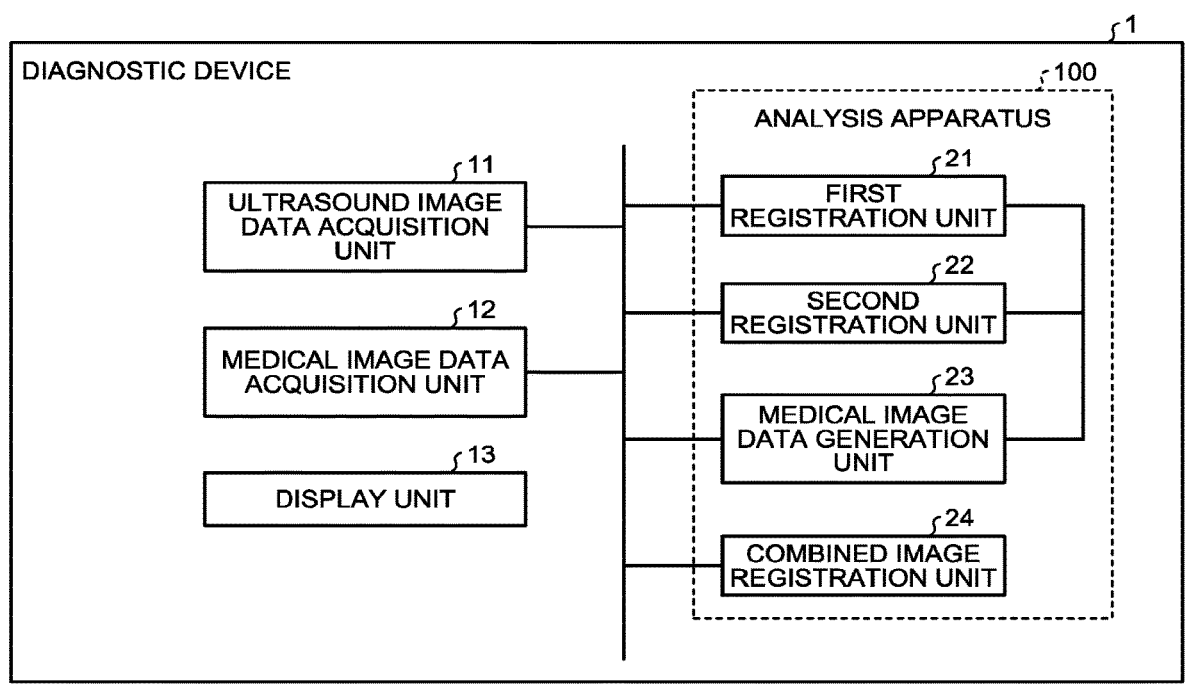
FIG. 1 is a diagram illustrating a configuration of an ultrasound diagnostic apparatus 1 according to an embodiment.

FIG. 1 shows a schematic configuration of an ultrasound diagnostic apparatus 1 of the present invention. As shown in FIG. 1, the ultrasound diagnostic apparatus 1 comprises: an ultrasound image data acquisition unit 11, a medical image data acquisition unit 12, a display unit 13, a first registration unit 21, a second registration unit 22, a medical image data generation unit 23, and a combined image registration unit 24. The first registration unit 21, the second registration unit 22, the medical image data generation unit 23, and the combined image registration unit 24 are implemented, for example, by a computer (processing circuitry) having a CPU and a memory. It is noted that the first registration unit 21, the second registration unit 22 and the medical image data generation unit 23 constitute the image generation unit.

It is noted that, as illustrated in FIG. 1, the first registration unit 21, the second registration unit 22, the image data generation unit 23 and the registration unit 24 may constitute the analysis apparatus 100. Such an analysis apparatus 100 obtain data from an ultrasound diagnostic apparatus or a medical image diagnostic apparatus, to function as an independent apparatus performing image process such as registration process. The analysis apparatus may be incorporated into the ultrasound diagnostic apparatus 1 or the medical image diagnostic apparatus, or an apparatus constructed independent of the ultrasound diagnostic apparatus 1 or medical image diagnostic apparatus.

In the embodiments, each processing function conducted by the processing circuitry of the computer by the first registration unit 21, the second registration unit, the image data generation unit 23 and the registration unit 24 is stored in the memory in the form of computer-executable programs. The processing circuitry is a processor realizing the function corresponding to each program by reading the program from the memory not illustrated and executing it. In other words, each of the first registration unit 21, the second registration unit 22, the image data generation unit 23, and the registration unit 24 is realized as processing circuitry having each of the first registration function, the second registration function, the image data generation function and the registration function, respectively. The processing circuitry in a state of having read each of the programs has each of these functions. It is noted that, in FIG. 1, it is explained that in FIG. 1, single processing circuitry realizes these functions, but a plurality of independent processors may be integrated into single processing circuitry and each processor realizes the function by executing each of the programs. In other words, each of the functions are constructed as programs and single processing circuitry executes each program.

The word "processor" in the explanation above means circuitry such as CPU (Central Processing Unit), GPU (Graphical Processing Unit), ASIC (Application Specific Integrated Circuit), Programmable Logic Device (e.g. SPLD (Simple Programmable Logic Device), CPLD (Complex Programmable Logic Device), FPGA (Field Programmable Gate Array)). The processor realizes the functions by reading and executing the programs stored in the memory.

The ultrasound image data acquisition unit 11 can acquire an ultrasound image by using a known structure, for example, by receiving echo of a living body part or tissue with an ultrasound probe (not shown). Ultrasound scan can acquire ultrasound images in real time and dynamically, and there is almost no damage to the living body, and the device is also easy to carry and move. The ultrasound image data acquired by the ultrasound image data acquisition unit 11 is transmitted to the first registration unit 21 and the second registration unit 22, which will be described later.

The medical image data acquisition unit 12 acquires image data including CT, MRI, and the like by X-ray or nuclear magnetic resonance, etc. . . . Taking MRI as an example, compared with ultrasound images, MRI has a higher soft tissue contrast resolution and can distinguish soft tissues such as muscles, tendons, fascia, and fat clearly. However, it takes a long time to acquire an MR image, and a special device is required, making it difficult to acquire image data in real time as the ultrasound diagnosis.

The first registration unit 21 and the second registration unit 22 register the image data. In particular, the first registration unit 21 registers the ultrasound image and the medical image data, and the second registration unit 22 registers the ultrasound images of different (time) phases. As an example of a medical image, the MR image is used in the present embodiment, but the present invention is not limited thereto, and it may be a CT image, an X-ray image, or the like. In the following description, the ultrasound image is sometimes referred to as a US (ultrasound) image, and the registration between the ultrasound image and the medical image data is referred to as US-MR image registration, and the registration between the ultrasound image and the medical image data is referred to as US-US image registration.

By performing US-MR image registration with the first registration unit 21, the registration between the ultrasound image and the MR image of the same phase can be obtained. For example, the first ultrasound image and the first MR image may be acquired in advance in a first phase before the diagnosis or treatment is started, and then the first ultrasound image and the first MR image may be registered. The first registration unit 21 generates a first registration parameter required for the registration between the first ultrasound image data and the first MR image data. In this way, the first registration unit 21 performs registration between the first ultrasound image data obtained at a first phase by the ultrasound diagnostic apparatus 1 and the first medical image data obtained from a medical diagnostic apparatus other than the ultrasound diagnostic apparatus 1.

By performing US-US image registration with the second registration unit 22, the registration between ultrasound images of different phases can be obtained. For example, the first ultrasound image may be acquired in the first phase before the diagnosis or treatment is started, and the second ultrasound image may be acquired in a second phase during diagnosis or treatment, and the registration between the first ultrasound image and the $n^{th}$ ultrasound image data can be obtained by the second registration unit 22. The second registration unit 22 generates a second registration parameter required for the registration between the first ultrasound image data and the second ultrasound image data. In this way, the second registration unit 22 performs registration between the first ultrasound image data and the second ultrasound image data. In this way, the second registration unit 22 performs registration between the first ultrasound image data and the second ultrasound image data obtained by the ultrasound diagnostic apparatus at a second phase different from the first time phase. It is noted that the second registration unit 22 performs registration, for example, between the first ultrasound image data and the second ultrasound image data, based on a value obtained from the detected position information of the ultrasound probe detected.

Detailed steps regarding the US-MR image registration and the US-US registration will be described later.

The medical image data generation unit 23, based on the first medical image acquired by the medical image data acquisition unit 12 in a first phase, the first registration parameter generated by the first registration unit 21, and the second registration parameter generated by the second registration unit, generates the second medical image data corresponding to (registered with) the second ultrasound image data. In particular, as described above, it is difficult to acquire MR image data in real time during diagnosis or treatment, and thus, using the first MR image data acquired before the diagnosis or treatment is started, and the first ultrasound image data and the second ultrasound image data that both can be acquired before and after the diagnosis or treatment is started, based on the first registration parameter between the first MR image data and the first ultrasound image data, and the second registration parameter between the first ultrasound image data and the second ultrasound image data, a third registration parameter between the first MR image data and the second US image data is generated. Further, the second MR image data is generated based on the first MR image data and the third registration parameter. By the process described above, the image data generation unit 23 generates second medical image data registered with the second ultrasound image data. Thus, the second MR image data corresponding to the phase of the second ultrasound image data can be generated quickly and accurately.

The image registration unit 24 registers and fuses the second MR image data generated by the medical image data generation unit 23 with the second ultrasound image data, and displays the registered and combined image on the display unit 13. In this way, the image registration unit 24 combines the second ultrasound image data and the second medical image data to generate a single image, thereby performing registration between ultrasound image data by the ultrasound diagnostic apparatus 1 and medical image data by the medical image diagnostic apparatus.

Next, the steps of generating the second MR image data will be described based on FIGS. 2 and 3.

First, in step S1, an MR imaging is performed and the first MR image data MR1 is generated (cf. FIG. 3(a)). Here, the phase in which the MR imaging is performed is, for example, a phase before the diagnosis or treatment.

Next, in step S2, an ultrasound scan is performed and the first US image data US1 is generated at a first phase (cf. FIG. 3(b)).

Next, in step S3, the US-MR registration process is performed on MR1 and US1 to generate a first registration parameter $T_{US1-MR1}$ between the first MR image data MR1 and the first US image data.

Next, after entering the diagnosis or treatment, in step S4, an ultrasound scan is performed and the $n^{th}$ US image data $US_n$ is generated at the $n^{th}$ phase (cf. FIG. 3(c)). Here, the number of the scan can be appropriately set, for example, as $2 \le n \le N$.

Next, in step S5, the US-US registration process is performed on US1 and USn to generate a second registration parameter $T_{US1-USn}$ between the first US image data US1 and the $n^{th}$ US image data USn.

Next, in step S6, a third registration parameter $T_{MS1-USn}$ between the first MR image data MR1 and the $n^{th}$ US image data USn is generated based on the first registration parameter $T_{US1-MR1}$ and the second registration parameter $T_{US1-USn}$.

Therefore, the registration relationship between the first MR image data MR1 and the $n^{th}$ US image data USn is established.

In particular, based on the second registration parameter $T_{US1-USn}$, a difference between the first US image data US1 and the $n^{th}$ US image data USn can be obtained. Further, the difference between the first US image data US1 and the $n^{th}$ US image data USn is converted into a difference between the first MR image data MR1 and the $n^{th}$ MR image data MRn. Here, actually, the $n^{th}$ MR image data MRn is not acquired by the medical image data acquisition unit 12.

Next, in step S7, MR image data MRn corresponding to the $n^{th}$ US image data USn is generated based on the first MR image data MR1 and the third registration parameters $T_{MR1-USn}$ (cf. FIG. 3(d)). Here, "corresponding" refers to US image data and MR image data of the same phase. Further, MRn is combined with USn to generate a single combined image.

Next, in step S8, it is confirmed whether or not the scan is completed. When the scan is completed, the process is terminated, and the combined image generated in step S7 is displayed on the display unit 13. If the scan is not completed, the process returns to step S4 and the process is repeated.

Thus, without performing MR scan in the $n^{th}$ phase, it is possible to generate the MR image data MRn of the $n^{th}$ phase indirectly based on the existing MR image data MR1, the ultrasound image data US1 of the same phase as MR1, and the ultrasound image data USn of the $n^{th}$ phase. Here, the US-MR registration process can be completed within 3 sec, and the US-US registration process can be completed within 1 sec. Therefore, it is possible to generate an MR image of an arbitrary phase very quickly and accurately, and it is possible to achieve an effect of providing an MR image in a near real time.

Figure 4:
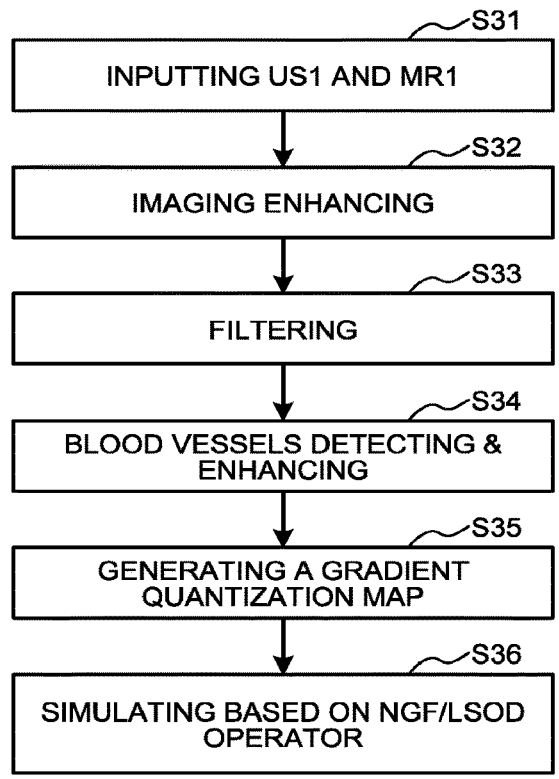
FIG. 4 is a flowchart illustrating the US-MR registration process according to the first embodiment.

In addition, FIG. 4 is a flowchart of the US-MR registration process.

Figure 5:
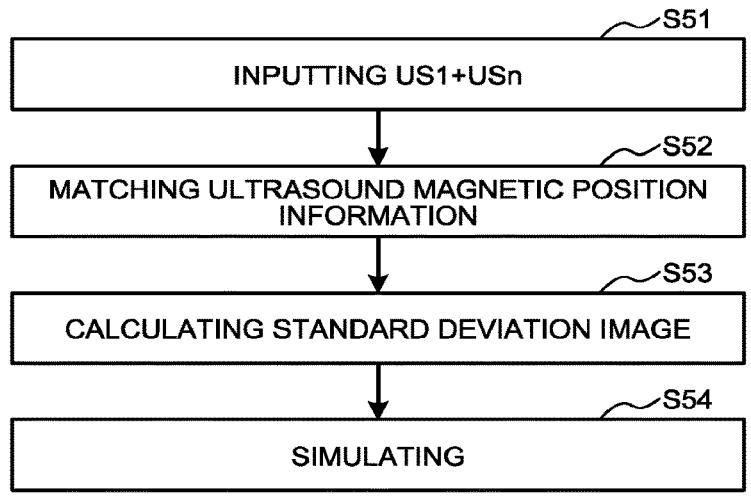
FIG. 5 is a flowchart illustrating the US-US registration process according to the first embodiment.

FIG. 5 is a flowchart of the US-US registration process.

Next, the technical effects of the present invention will be described. In the past, MR scans were necessary if real-time MR images were required during diagnosis or treatment. However, the acquisition of the MR image takes a long time and requires special equipment, making it difficult to acquire image data in a convenient and real-time manner as the ultrasound diagnosis. Here, according to the present invention, MR images of an arbitrary phase are not scanned and generated directly, but MR images MR1 and US images US1 of a certain phase are acquired in advance before the diagnosis or treatment, and they are registered to obtain the registration parameters therebetween. Next, a US image USn of a certain phase is acquired during diagnosis or treatment, and US1 and USn are registered to obtain the registration parameters therebetween. Thus, the registration parameters between the MR image MR1 before the diagnosis or treatment is started and the MR image MRn after the diagnosis or the treatment is started can be obtained via US1. Based on the registration parameters, the MR image MRn corresponding to USn, that is, having the same phase as USn, can be generated. In addition, as described above, the US-MR registration process can be completed within 3 sec, and the US-US registration process can be completed within 1 sec.

In this way, without MR scan, the MR image data can be acquired indirectly and MR image data of an arbitrary phase can be generated at low cost and quickly for reference by a physician or the like.

Next, detailed steps of the US-MR registration process in step S3 will be described in detail with reference to FIG. 4.

First, in step S31, the first US image data US1 and the first MR image data MR1 are input.

Next, in step S32, image enhancement is performed on the first US image data US1 and the first MR image data MR1.

Next, in step S33, the first US image data US1 and the first MR image data MR1 are filtered to remove noise or useless images interfering with the registration.

Next, in step S34, blood vessel detection is performed and the blood vessel image is enhanced. In the present invention, the registration process is based on the blood vessels.

Next, in step S35, a gradient quantization map is generated.

Next, in step S36, simulation is performed based on the gradient quantization map generated in step S35 and the NGF operator or the LSOD operator, so as to perform US-MR registration process to generate a first registration parameter $T_{US1-MR1}$ between the first MR image data MR1 and the first US image data.

Next, detailed steps of the US-US registration process in step S5 will be described with reference to FIG. 5.

First, in step S51, the first US image data US1 and the $n^{th}$ US image data USn are input.

Next, in step S52, the ultrasound magnetic position information is matched, and the first US image data US1 and the $n^{th}$ US image data USn are matched, to obtain a difference between the first US image data US1 and the $n^{th}$ US image data USn.

Next, in step S53, a standard deviation image is calculated based on the matching result of step S52.

Next, in step S54, the second registration parameter $T_{US1-USn}$ between the first US image data US1 and the $n^{th}$ US image data USn are obtained based on the simulation result.

Second Embodiment

In the first embodiment, at Step S3, the first registration unit 21 performs registration between the first ultrasound image obtained at the first phase and the first medical image data (for example, MR image data). Further, at Step S5, the second registration unit 22 performs registration between the first ultrasound image obtained at the first phase and the second ultrasound image obtained at a phase different from the first phase, that is, for example, the second phase. Further, a case is explained in which, at Step S6 and Step S7, the image data generation unit 23 generates the second medical image data registered with the second ultrasound image data, based on the result of registration at Step S3 or S5. In the second embodiment, a case is explained in particular in which three-dimensional image data is used for the registration.

Figure 2:
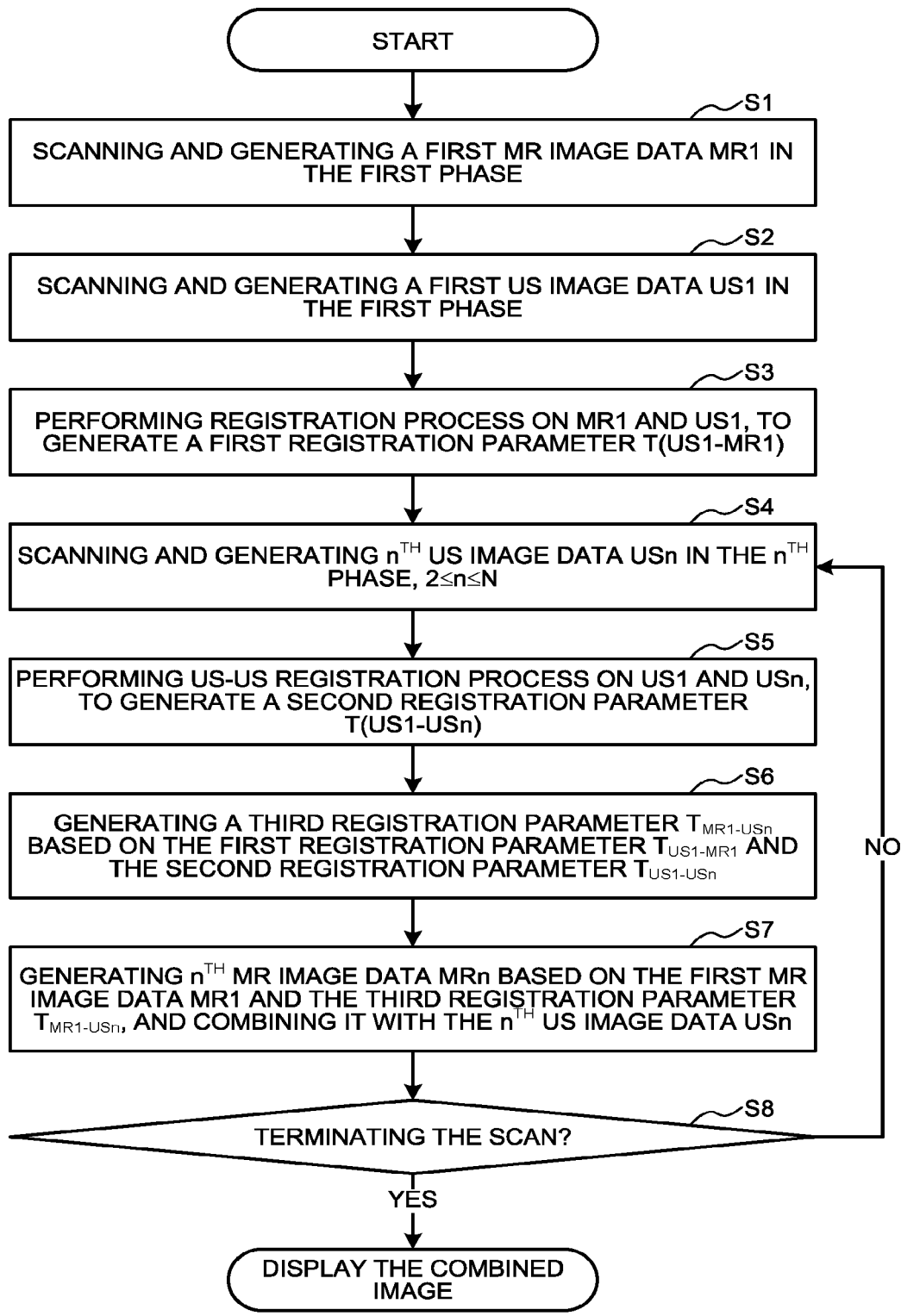
FIG. 2 is a flowchart illustrating a procedure of generation process of an MR (Magnetic Resonance) image of an arbitrary time phase according to the first embodiment.
Figure 3:
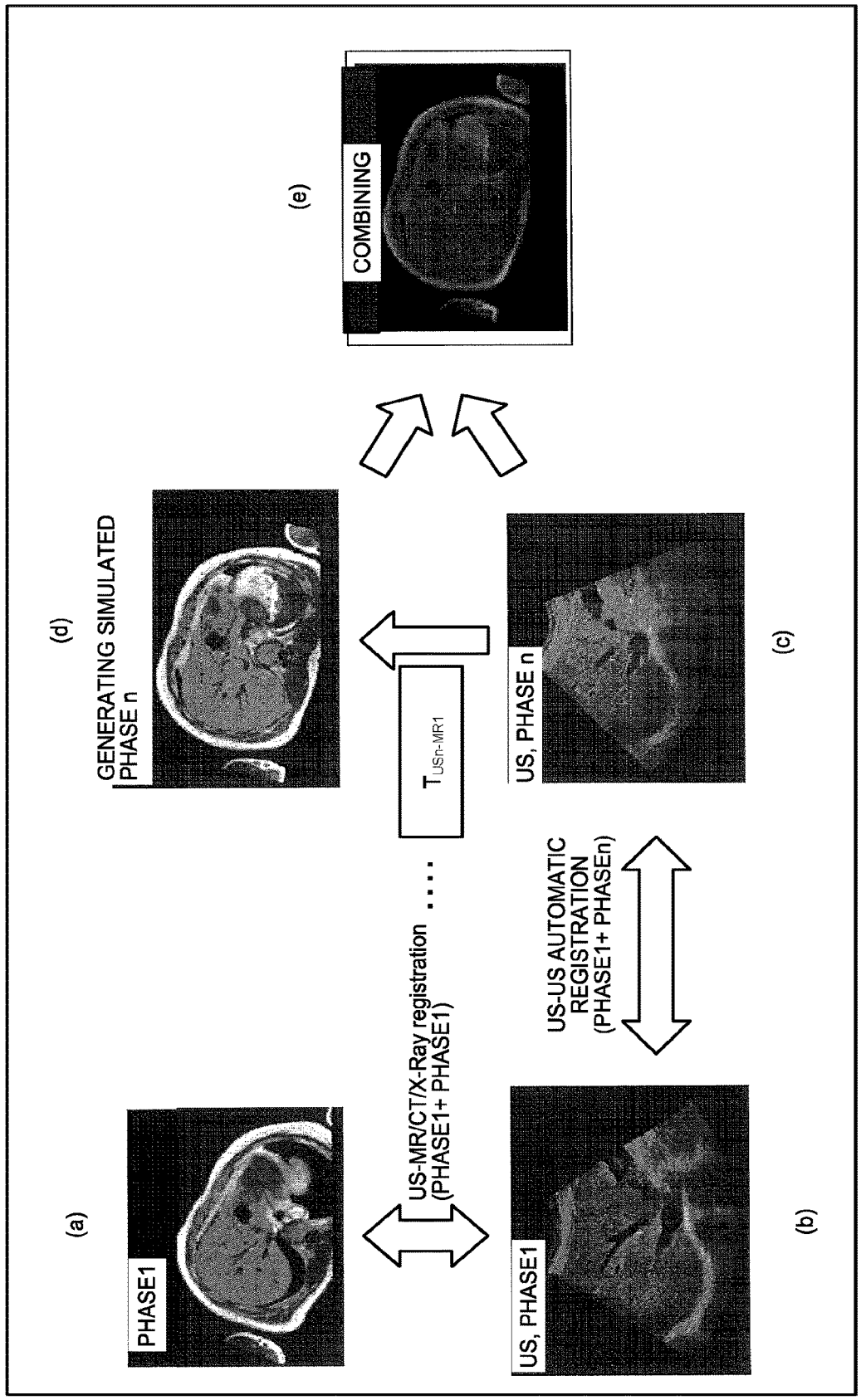
FIG. 3 is a diagram illustrating a registration process of an ultrasound image and an MR image according to the first embodiment.
Figure 6:
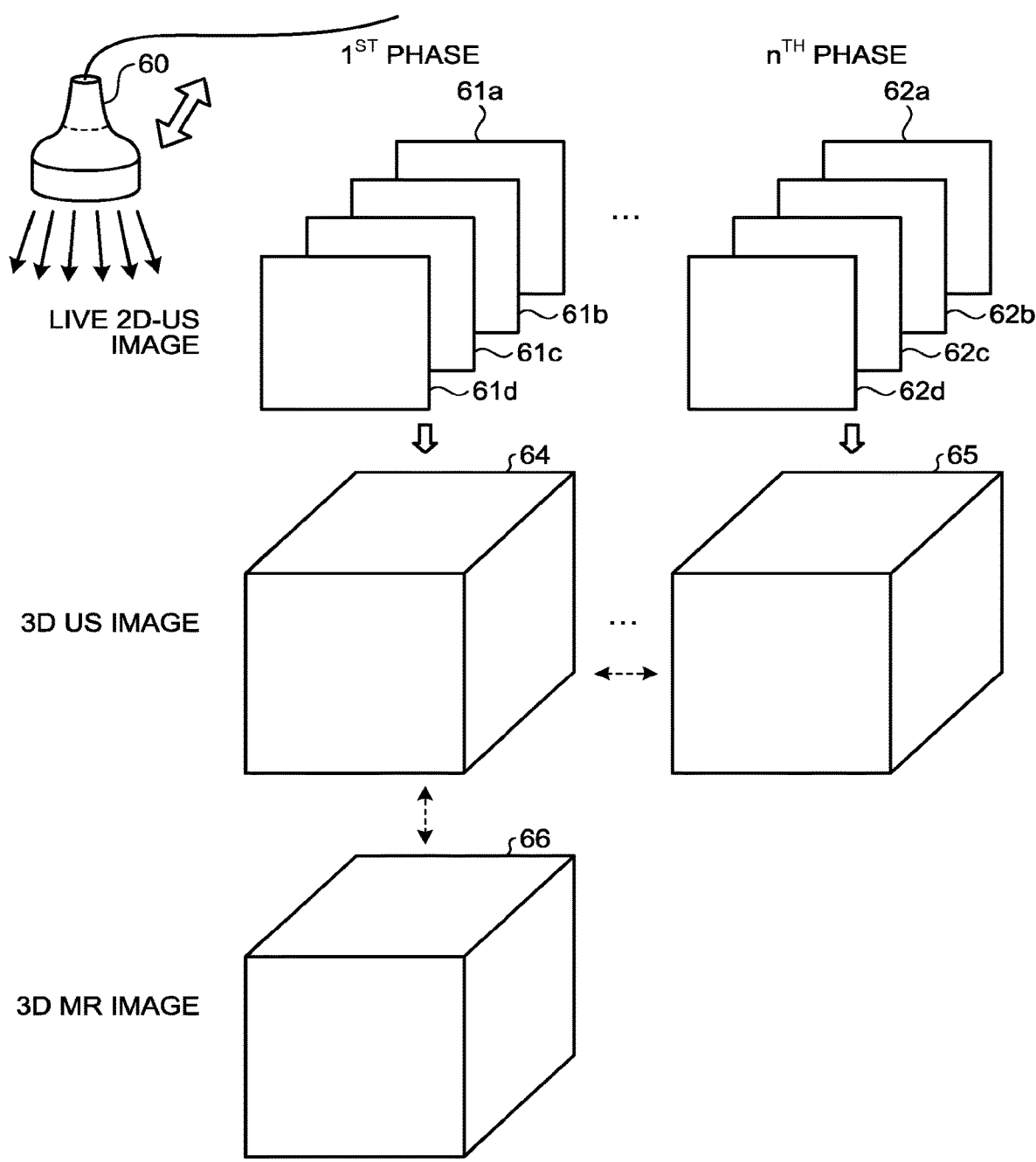
FIG. 6 is a diagram illustrating a process according to a second embodiment.

By using again the flowchart of FIG. 2 and with reference to FIG. 6, the flow of process conducted by the ultrasound diagnostic apparatus according to the second embodiment is explained. FIG. 6 is a diagram illustrating processing according to the second embodiment.

At Step S1, a magnetic resonance imaging apparatus, which is an example of a medical image diagnostic apparatus, performs magnetic resonance imaging to generate three-dimensional MR image 66. The medical image data acquisition unit 12 obtains three-dimensional MR image 66 from the medical image diagnostic apparatus. In other words, the three-dimensional MR image 66, which is a first medical image data obtained by the medical image diagnostic apparatus, is three-dimensional image data.

Next, at Step S2, the ultrasound image data acquisition unit 11 obtains, by the ultrasound probe 60, at the first phase, a plurality of two-dimensional ultrasound image data. For example, the ultrasound image data acquisition unit 11 obtains a plurality of Live 2D images 61a, 61b, 61c, 61d and the like at the first phase, by manipulating the ultrasound probe 6 in a slice direction (a direction perpendicular to the sheet of FIG. 6), which is a direction perpendicular to the two-dimensional plane made of an axial direction (the up-bottom direction of FIG. 6) and a lateral direction (the left-right direction of FIG. 6). Next, the ultrasound image data acquisition unit 11 obtains the three-dimensional ultrasound image data as the first ultrasound image data, from the plurality of two-dimensional ultrasound image data obtained at the first phase. For example, the ultrasound image data acquisition unit reconstructs, from the plurality of Live 2D images 61a, 61b, 61c, 61d and the like obtained at the first phase, based on the position information obtained from the magnetic position sensor included in the ultrasound probe 60, three-dimensional ultrasound image data 64.

Next, at Step S3, the first registration unit 21 performs registration between the three-dimensional ultrasound image data 64 that is the first ultrasound image data and the three-dimensional MR image 66 that is the first medical image data. The details of the registration process are already explained in FIG. 4.

Similarly to Step S2, at Step S4, the ultrasound image data acquisition unit 11 obtains a plurality of Live 2D images 62a, 62b, 62c, 62d and the like at the n-th phase, with the user performing the similar operation as the first phase at phases other than the first phase. Next, the ultrasound image data acquisition unit 11 reconstructs, from the plurality of two-dimensional ultrasound image data obtained at the n-th phase (the second phase, the third phase, . . . ), a three-dimensional ultrasound image data. For example, the ultrasound image data acquisition unit reconstructs, from the plurality of Live 2D images 62a, 62b, 62c, 62d and the like obtained at the n-th phase, based on position information obtained from magnetic position sensor included in the ultrasound probe 62, three-dimensional ultrasound image data 65.

Next, at Step S5, the second registration unit 22 performs registration between the three-dimensional ultrasound image data 64 that is the first ultrasound image data at the first phase and the three-dimensional ultrasound image that is ultrasound image data obtained at the n-th phase (the second phase, the third phase . . . ). The details of the registration are already explained in FIG. 5.

Next, at Step S6, the image data generation unit 23 performs the process similar to the first embodiment, to generate medical image data at the n-th phase (the second phase, the third phase), thereby generating medical image data registered with the ultrasound image data at the n-th phase. The details of the registration are already explained in FIG. 3 and the like.

Next, at Step S7, the registration unit 24 performs process similar to the first embodiment to perform registration. The following processes of Step S4 to S8 are performed until the scan is finished.

In the second embodiment, the registration is performed between the three-dimensional ultrasound image data and the three-dimensional medical image data, in other words, between a plurality of pieces of three-dimensional image data.

Here, an advantage of using a plurality of pieces of three-dimensional image data to perform registration is the following. In other words, when performing registration between a plurality of pieces of two-dimensional image data, in the first place, the plurality of pieces of two-dimensional image data that are subject to registration are not necessarily completely parallel planes and sometimes they are unsuitable data sets for registration. For example, sometimes, the plane in which the ultrasound scan is performed may be the plane of inappropriate angles as time goes by. Therefore, according to the ultrasound diagnostic apparatus 1 and the analysis apparatus 100 according to the second embodiment, by performing registration between a plurality of pieces of three-dimensional image data, registration can be appropriately performed regardless of the angle of the plane in which the ultrasound scan is performed.

Embodiments are not limited to the case described above. For example, the analysis apparatus 100 may perform registration between a plurality of pieces of MPR (Multi Planar Reconstruction) image data, for example, between an MR-MPR image and an US-MPR image, or an MR-MPR image and an US-Live 2D image, instead of using a plurality of three-dimensional image data.

According to an analysis apparatus according to at least one embodiment described above, it is possible to perform registration between medical images.

Further, the image generation unit corresponds to the first registration unit 21, the second registration unit 22, and the image data generation unit 23 and the image registration unit corresponds to the registration unit 24.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An analysis apparatus comprising:
   processing circuitry configured to:
   perform registration between first ultrasound image data obtained at a first phase by an ultrasound diagnostic apparatus and first medical image data obtained by a medical image diagnostic apparatus other than the ultrasound diagnostic apparatus and perform registration between the first ultrasound image data and second ultrasound image data obtained at a second phase different from the first phase by the ultrasound diagnostic apparatus, to generate second medical image data registered with the second ultrasound image data; and combine the second ultrasound image data and the second medical image data to generate a single image, thereby performing registration between ultrasound image data by the ultrasound diagnostic apparatus and medical image data by the medical image diagnostic apparatus, wherein the first medical image data is three-dimensional image data, the first ultrasound image data is three-dimensional image data constructed from a plurality of two-dimensional ultrasound image data obtained at the first phase, the plurality of two-dimensional ultrasound image data being obtained by manipulating an ultrasound probe in a slice direction which is a direction perpendicular to a two-dimensional plane made of an axial direction and a lateral direction, and the second ultrasound image data is three-dimensional ultrasound image data constructed from a plurality of two-dimensional ultrasound image data obtained at the second phase.

2. The analysis apparatus according to claim 1, wherein the processing circuitry is configured to perform registration between the first ultrasound image data and the second ultrasound image data, based on a value obtained from detected position information of the ultrasound probe.

3. The analysis apparatus according to claim 1, wherein the second phase is a phase before diagnosis or treatment.

4. The analysis apparatus according to claim 1, wherein the medical image data is at least one of MRI (Magnetic Resonance Imaging) data, CT (Computed Tomography) image data and X-ray image data.

5. An ultrasound diagnostic apparatus comprising:
processing circuitry configured to:
obtain first ultrasound image data at a first phase and second ultrasound image data at a second phase different from the first phase;
perform registration between the first ultrasound image data and first medical image data obtained by a medical image diagnostic apparatus and configured to perform registration between the first ultrasound image data and the second ultrasound image data, to generate second medical image data registered with the second ultrasound image data; and
combine the second ultrasound image data and the second medical image data to generate a single image, thereby performing registration between ultrasound image data by the ultrasound diagnostic apparatus and medical image data by the medical image diagnostic apparatus, wherein the first medical image data is three-dimensional image data, the first ultrasound image data is three-dimensional image data constructed from a plurality of two-dimensional ultrasound image data obtained at the first phase, the plurality of two-dimensional ultrasound image data being obtained by manipulating an ultrasound probe in a slice direction which is a direction perpendicular to a two-dimensional plane made of an axial direction and a lateral direction, and the second ultrasound image data is three-dimensional ultrasound image data constructed from a plurality of two-dimensional ultrasound image data obtained at the second phase.

6. The ultrasound diagnostic apparatus according to claim 5, wherein the processing circuitry is configured to perform registration between the first ultrasound image data and the second ultrasound image data, based on a value obtained from detected position information of the ultrasound probe.

7. The ultrasound diagnostic apparatus according to claim 5, wherein the second phase is a phase before diagnosis or treatment.

8. An analysis method comprising:
performing, by processing circuitry, registration between first ultrasound image data obtained at a first phase by an ultrasound diagnostic apparatus and first medical image data obtained by a medical image diagnostic apparatus other than the ultrasound diagnostic apparatus and performing, by the processing circuitry, registration between the first ultrasound image data and second ultrasound image data obtained at a second phase different from the first phase by the ultrasound diagnostic apparatus, to generate second medical image data registered with the second ultrasound image data; and
combining, by the processing circuitry, the second ultrasound image data and the second medical image data to generate a single image, thereby performing registration between ultrasound image data by the ultrasound diagnostic apparatus and medical image data by the medical image diagnostic apparatus, wherein the first medical image data is three-dimensional image data, the first ultrasound image data is three-dimensional image data constructed from a plurality of two-dimensional ultrasound image data obtained at the first phase, the plurality of two-dimensional ultrasound image data being obtained by manipulating an ultrasound probe in a slice direction which is a direction perpendicular to a two-dimensional plane made of an axial direction and a lateral direction, and the second ultrasound image data is three-dimensional ultrasound image data constructed from a plurality of two-dimensional ultrasound image data obtained at the second phase.

* * * * *